United States Patent
Meier et al.

(10) Patent No.: US 6,399,543 B1
(45) Date of Patent: Jun. 4, 2002

(54) LOW FOAM N,N'-DIALKYLTARTARAMIDE WETTING AGENTS

(75) Inventors: Ingrid Kristine Meier, Asbury, NJ (US); Kevin Rodney Lassila, Macungie; Caroline Sassano Slone, Quakertown, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/820,400

(22) Filed: Mar. 29, 2001

(51) Int. Cl.$^7$ .................. A01N 25/30; C09D 11/02; C09D 5/02; C09J 11/06; G03F 7/32
(52) U.S. Cl. .................. 504/362; 514/788; 514/975; 106/31.13; 106/124.1; 438/906; 516/203; 510/128
(58) Field of Search ............ 504/362; 514/975, 514/788; 106/31.13, 124.1; 438/906; 516/203; 510/128

(56) References Cited

U.S. PATENT DOCUMENTS

| | | | |
|---|---|---|---|
| 4,782,005 A | 11/1988 | Eklund et al. | 430/284 |
| 5,776,494 A | 7/1998 | Guskey et al. | 424/484 |
| 6,281,170 B1 * | 8/2001 | Marsella et al. | 504/362 |

FOREIGN PATENT DOCUMENTS

| | | |
|---|---|---|
| DE | 4041184 | 6/1992 |
| DE | 4424533 | 1/1996 |

OTHER PUBLICATIONS

Padget, J. C., "Additives for Water–Based Coatings—A Polymer Chemist's View", Additives for Water–Based Coatings, D. R. Karsa, ed., Cambridge UK: Royal Society of Chemistry, 1990, pp. 1–29.

Dispersions: Characterization, Testing and Measurement, Marcel Dekker, Inc. 1990 pp. 137–172.

Kubler, R., "Printing Inks" Ulmann's Encyclopedia of Industrial Chemistry, vol. A22, 1993, pp. 143–156.

Bassemir, R. W., et al., "Inks" Kirk–Othmer Encyclopedia of Chemical Technology, 4$^{th}$ Edition, vol. 14, pp. 482–503.

Sheats, J., R., Smith, B. W. "Microlithography, Science and Technology" Marcel Dekker, Inc. 1998, pp. 551–553.

Konig, et al., "Synthesis", Dec., 1993, pp. 1233–1234.

Dermer and George, "Proceedings of the Oklahoma Academy of Science", 1972, 52 pp. 66–69.

* cited by examiner

Primary Examiner—S. Mark Clardy
(74) Attorney, Agent, or Firm—Michael Leach

(57) ABSTRACT

This invention provides water-based compositions, particularly coating, ink, fountain solution, adhesive, agricultural and electronics cleaning compositions, manifesting reduced equilibrium surface tension by the incorporation of a surface tension reducing amount of an N,N'-dialkylamide of tartaric acid of the following structure:

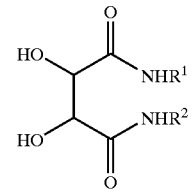

where $R^1$ and $R^2$ are C4 to C8 alkyl groups with at least one of $R^1$ and $R^2$ being a branched C4 to C8 alkyl group.

25 Claims, No Drawings

LOW FOAM N,N'-DIALKYLTARTARAMIDE WETTING AGENTS

FIELD OF THE INVENTION

The invention relates to the use of dialkyltartaramides to reduce the surface tension in water-based systems.

BACKGROUND OF THE INVENTION

The ability to reduce the surface tension of water is of great importance in waterborne coatings, inks, adhesives, fountain solutions and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important measure of the ability of a surfactant to reduce surface tension in aqueous systems when the system is at rest.

Traditional nonionic surfactants, such as alkylphenol or alcohol ethoxylates and ethylene oxide (EO)/propylene oxide (PO) copolymers, and anionic surfactants, such as sodium dialkyl sulfosuccinates, have good equilibrium surface tension performance. However, many of these surfactants are foamy and this can lead to problems in applications such as coatings, inks, adhesives, fountain solutions, agricultural formulations, electronic chemicals and cleaning formulations, and other applications where foam can lead to surface defects, poor adhesion, and processing difficulties. Additionally, anionic surfactants can impart water sensitivity to the finished coating.

In addition to the development of high-performance surfactants, there is considerable interest in the industry in surfactants with improved environmental characteristics. Environmental concerns have led to an increased use of environmentally compatible surfactants as alternatives have become available. In addition, the use of less favorable products, such as alkylphenol ethoxylate (APE) surfactants, has declined. This is, in part, due to the poor environmental characteristics of APE surfactants, such as incomplete biodegradation and a suspicion that they may function as endocrine mimics. The demand for high-performance, eco-friendly surfactants has stimulated efforts in new surfactant development. From this work a new family of surfactants, referred to as alkyl polyglycoside (APG) surfactants, has emerged as a readily biodegradable. environmentally-friendly alternative to conventional surfactants. These materials can be foamy and thus are not suitable for many coating, ink, adhesive, fountain solution, agricultural, and electronic chemical and cleaning applications where the generation of foam is undesirable.

Thus, not only is it desirable to obtain surfactants which exhibit excellent surface tension reducing capabilities and low foam, but it is also highly desirable that such new surfactants are environmentally-friendly. Moreover, since there is substantial interest in the development of environmentally-friendly surfactants. an essential attribute would be that these new surfactants not only possess the aforementioned desired performance properties but also are derived from naturally occurring compounds or their synthetic equivalents.

The importance of reducing surface tension in applications such as coatings, inks, adhesives, agricultural formulations, and electronic chemical and cleaning is well-appreciated in the art. The ability to lower the surface tension of aqueous media without producing foam is critical when one wants to wet low energy or contaminated substrates. In J. C. Padget's article entitled "Additives for Water-based Coatings—A Polymer Chemist's View" in *Additives for Water-based Coatings*, D. R. Karsa, ed., Cambridge, UK: Royal Society of Chemistry, 1990, pp. 1–29, the importance of surfactants in lowering the surface tension of aqueous systems in order to achieve wetting on low energy materials such as plastics and oily steel is highlighted.

In the graphic arts, it is well-known that surfactants lower the surface tension of aqueous media and thus aid in printing on lower energy substrates such as plastics, coated papers, coated cardboards, and foils and in wetting pigments to produce dispersions. In *Dispersions: Characterization, Testing, and Measurement*, Marcel Dekker, Inc., 1990, there is an entire chapter devoted to the topic of wettability and the necessity of lowering surface tension in order to achieve displacement of air from around small pigment particles and allow wetting and spreading on the pigment surface. Surfactants are known to act as wetting agents to moisten hydrophobic areas of the printing plate in offset printing (R. Kubler, "Printing Inks," in *Ullmann's Encyclopedia of Industrial Chemistry*, Vol. A22, 1993, pp. 143–156), and certain surfactants have been beneficial in reducing foam generation in the ink fountain in flexographic and rotogravure printing inks (R. W. Bassemir, et al. "Inks," in *Kirk-Othmer Encyclopedia of Chemical Technology*, 4th Edition, Vol. 14, pp. 482–503).

In addition, the demands of the semiconductor fabrication industry have led to the requirement for high performance surfactants and wetting agents for photoresist developer formulations. As line features shrink to smaller sizes and photoresist substrate materials become more aliphatic in nature (i. e., lower surface energy), aqueous developer solutions increasingly are being formulated with surface tension reducing agents. An additional requirement for these developers, accentuated by the move toward larger wafer sizes, is that they exhibit low foam. This is particularly important when the so-called spray puddle techniques are used in applying the developer solution, wherein the developer is sprayed over increasingly larger areas. Even in cases where puddle or immersion techniques are used, microbubble entrainment during spreading of the solution over the photoresist surface can lead to defects. Other applications in the electronics industry using aqueous processing media would also benefit from good wetting and low foam.

Tetramethylammonium hydroxide (TMAH) is the chemical of choice in aqueous alkaline solutions for developing photoresists according to Microlithography, Science and Technology, J. R. Sheats and B. W. Smith, editors, Marcel Dekker, Inc., 1998, pp. 551–553. Surfactants are added to the aqueous TMAH solutions to reduce development time and scumming and to improve surface wetting.

Amides of tartaric acid (2,3-dihydroxy butanedioic acid), also called tartaramides, are known. L-Tartaric acid occurs naturally in grapes and is produced from the residues deposited in fermentation vats during wine making. It is classified as GRAS (Generally Recognized As Safe) by the U.S. Food and Drug Administration and is commonly used by the food, pharmaceutical and viniculture industries. The racemic form, DL-tartaric acid, is also known. It is produced by maleic acid oxidation or L-tartaric acid racemization.

In the literature, tartaric acid amides are known. However, the ability of tartaramides to lower surface tension in aqueous media has not been realized.

U.S. Pat. No. 4,782,005 discloses the use of certain N,N'-dialkyl tartaramides, in which the alkyl groups contain from 2 to 20 carbon atoms, as additives for decreasing the oxygen inhibition of the ultraviolet light radiation sensitive acrylic or methacrylic acid esters.

Synthesis, December, 1993, pp. 1233–1234, Konig, et. al., discloses the preparation of N,N'-bis-(tert-butyl) tartaramide for use as an intermediate in the preparation of N-tert-butylglyoxylamide. The reaction is achieved using 2 equivalents of $NaIO_4$ and 11 equivalents of water in 60 equivalents methylene chloride solution.

Proceedings of the Oklahoma Academy of Science, 1972, 52, pp. 66–69, Dermer and George, discloses the preparation of several tartaramides via reaction of the tartrate esters with primary amines. Tartaramides based on methyl, ethyl, n-butyl, cyclohexyl, and hydroxyethyl amines were isolated and characterized.

DE 4424533 A1 discloses oligohydroxy dicarboxylic acid derivatives, including certain tartaramides derived from fatty alkyl amines, as synthetic barrier lipids in skin care products.

DE 4041184 A1 discloses the use of C1–C26 amides of tartaric acid as oil defoamers in paper manufacturing.

U.S. Pat. No. 5,776,494 discloses the use of alkyl amides of di- and tri-carboxylic acids as gelling agents in pharmaceutical compositions.

SUMMARY OF THE INVENTION

This invention provides water-based compositions containing an organic or inorganic compound. particularly aqueous organic coating, ink, adhesive, fountain solution, agricultural and electronics cleaning compositions, having reduced surface tension by incorporation of an effective amount of an N,N'-dialkylamide of tartaric acid, herein referred to as a tartaramide, of the following structure:

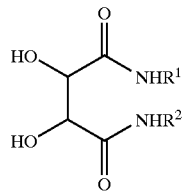

where $R^1$ and $R^2$ are C4 to C8 alkyl groups, and at least one of $R^1$ and $R^2$ is a branched C4 to C8 alkyl group. It is also desirable that an aqueous solution of the tartaramide demonstrate an equilibrium surface tension of less than 52 dynes/cm at a concentration of no more than 5 wt % in water at 25° C. using the Wilhelmy plate method. The Wilhelmy plate method of measuring surface tension is described in L. Wilhelmy's article in Ann. Phys. 1863, 119, 177, which is incorporated by reference.

By "water-based", "aqueous" or "aqueous medium", we mean, for purposes of this invention, a solvent or liquid dispersing medium which comprises at least 90 wt %, preferably at least 95 wt %, water. Obviously, an all water medium is also included.

Also provided is a method for lowering the equilibrium surface tension of such aqueous compositions by the incorporation of these tartaramide compounds.

Also provided is a method for applying a coating of a water-based inorganic or organic compound-containing composition to a surface to partially or fully coat the surface with the water-based composition, the composition containing an effective amount of a tartaramide compound of the above structure for reducing the equilibrium surface tension of the water-based composition.

There are significant advantages associated with the use of these tartaramides in water-based, organic-compound containing compositions, such as water-based coatings, inks, adhesives, fountain solutions, agricultural formulations, and electronic chemical and cleaning formulations, including photoresist developer compositions, and these advantages include:

water-borne coatings, inks, adhesives, fountain solutions, agricultural formulations. and electronic chemical formulations which may be applied to a variety of substrates with excellent wetting of substrate surfaces;

a reduction in coating or printing defects such as orange peel and flow/leveling deficiencies;

low surface tension aqueous electronics cleaning and processing solutions, including photoresist developer solutions, which provide good wetting and very low foam;

low-foam surfactants capable of reducing surface tension;

water-borne compositions using a surfactant derived from natural, renewable resources, thus making such formulations environmentally favorable.

Because of their surfactant properties and the ability to control foam, these materials are likely to find applicability in many applications in which the reduction in surface tension and low foam are important. Such applications in which low foam is important include various wet-processing textile operations, such as the dyeing of fibers, fiber scouring, and kier boiling, where low-foaming properties would be particularly advantageous; they may also have applicability in soaps, water-based perfumes, shampoos, detergents, cosmetics and food processing where their marked ability to lower surface tension, and at the same time produce little to no foam would be highly desirable.

DETAILED DESCRIPTION OF THE INVENTION

This invention relates to the use of N,N'-dialkylamide compounds of the structure:

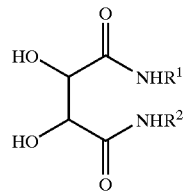

where $R^1$ and $R^2$ are C4–C8 alkyl groups, and at least one of $R^1$ and $R^2$ is a branched C4 to C8 alkyl group, preferably C5 to C8, and most preferably C6 to C8, for the reduction of equilibrium surface tension in water-based compositions containing an organic compound, particularly coating, ink, fountain solution, adhesive, agricultural, and photoresist developer compositions containing organic compounds such as polymeric resins, detergents, herbicides, fungicides, insecticides or plant growth modifying agents. It is also desirable that an aqueous solution of the tartaramide demonstrate an equilibrium surface tension of less than 52 dynes/cm at a concentration of 5 wt % or less in water at 25° C. using the Wilhelmy plate method.

In one aspect of the invention the tartaramides of the above formula display excellent ability to reduce equilibrium surface tension while producing little to no foam.

These materials may be prepared by the reaction of primary amines with tartaric acid or tartaric acid esters. The reaction is illustrated below:

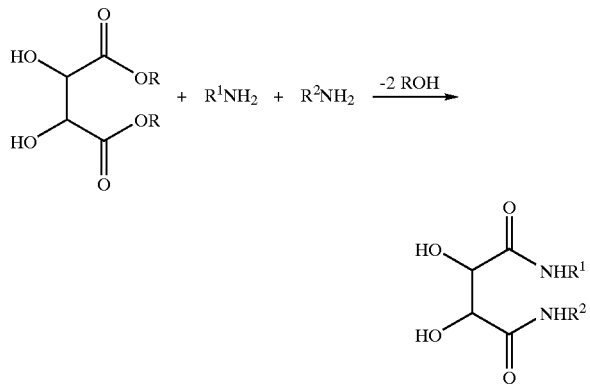

The amination reaction may be performed using a variety of conditions as described in the *Kirk-Othmer Encyclopedia of Chemical Technology*, 4th Ed., Vol. 2, pp. 348–351. The preferred method involves the reaction of a tartaric acid ester with 2 or more equivalents amine in a protic solvent.

All primary amines or mixtures of primary amines containing at least one C4 to C8 branched alkyl amine may be utilized for the preparation of the N,N'-dialkyl-tartaramides of this invention, with amines containing 5–8 carbon alkyl groups being preferred and those containing 6–8 carbons being especially preferred. The N,N'-dialkyltartaramides may contain a total of 8–16 amide alkyl carbon atoms, with those containing a total of 10–16 amide alkyl carbons being preferred and those containing a total of 12–16 amide alkyl carbons being especially preferred. Alkyl groups which are suitable should have sufficient carbon to confer surface activity (i.e. an ability to reduce the surface tension of water) to the material but not enough carbon to decrease the solubility to the extent that the ability of the material to reduce surface tension is insufficient for a particular application. Generally, in the practice of this invention, it is desirable to choose amide alkyl groups such that the resulting N,N'-dialkyltartaramides have a solubility that affords the desired surface tension reduction.

The alkyl groups in the tartaramides of this invention may be the same or different and may be linear or branched, as long as at least one of the alkyl groups is a branched alkyl group. Examples of suitable branched alkyl groups are isobutyl, sec-butyl, 2-pentyl, 3-pentyl, isopentyl, neopentyl, 2-methylbutyl, 3-methyl-2-butyl, 2-hexyl, 3-hexyl, 2-ethylbutyl, 4-methyl-2-pentyl, 2-ethylhexyl, 1-methylhexyl, 1,5-dimethylhexyl, 1-methyl-heptyl, and so on. Of the tartaramide derivatives those which contain a total of 8 to 16 amide alkyl carbons are preferred and those containing 10 to 16 alkyl carbons most preferred, especially in the cases where $R^1=R^2=$1,5-dimethylhexyl, 2-ethylhexyl, 1-methylhexyl, and 1-methylheptyl.

An amount of N,N'-dialkyltartaramide compound that is effective to reduce the equilibrium surface tension of the water-based, inorganic or organic compound-containing composition is added. Such effective amount may range from 0.001 to 20 wt %, preferably 0.01 to 10 wt %, and most preferably 0.05 to 5 wt %, of the aqueous composition. Naturally, the most effective amount will depend on the particular application and the solubility of the tartaramide.

The dialkyltartaramides are suitable for use in an aqueous composition comprising in water an inorganic compound which is a mineral ore or a pigment or an organic compound which is a pigment, a polymerizable monomer, such as addition, condensation and vinyl monomers, an oligomeric resin, a polymeric resin, a detergent, a caustic cleaning agent, a herbicide, a fungicide, an insecticide, or a plant growth modifying agent.

In the following water-based organic coating, ink, adhesive, fountain solution, agricultural and photoresist developer compositions containing a dialkyltartaramide according to the invention, the other listed components of such compositions are those materials well known to the workers in the relevant art.

A typical water-based protective or decorative organic coating composition to which the dialkyltartaramide surfactants of the invention may be added would comprise in an aqueous medium 30 to 80 wt % of a coating composition containing the following components:

| Water-Based Organic Coating Composition | |
| --- | --- |
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvent |
| 0.01 to 10 wt % | Surfactant/Wetting Agent/Flow and Leveling Agents |
| 0.01 to 5 wt % | Dialkyltartaramide |

A typical water-based ink composition to which the dialkyltartaramide surfactants of the invention may be added would comprise in an aqueous medium 20 to 60 wt % of an ink composition containing the following components:

| Water-Based Ink Composition | |
| --- | --- |
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing or Other Solvent |
| 0.01 to 10 wt % | Surfactant/Wetting Agent |
| 0.01 to 10 wt % | Processing Aids/Defoamers/Solubilizing Agents |
| 0.01 to 5 wt % | Dialkyltartaramide |

A typical water-based agricultural composition to which the dialkyltartaramide surfactants of the invention may be added would comprise in an aqueous medium 0.01 to 80 wt % of an agricultural composition containing the following components:

| Water-Based Agricultural Composition | |
| --- | --- |
| 0.1 to 50 wt % | Pesticide, Insecticide, Herbicide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.01 to 50 wt % | Dialkyltartaramide |

A typical water-based fountain solution composition for planographic printing would comprise the following components:

| Water-Based Fountain Solution | |
|---|---|
| 0.05 to 10 wt % | Film formable, water soluble macromolecule |
| 1 to 25 wt % | Alcohol, glycol, or polyol with 2–12 carbon atoms, water soluble or can be made to be water soluble |
| 0.01 to 20 wt % | Water soluble organic acid, inorganic acid, or a salt thereof |
| 30 to 70 wt % | Water |
| 0.01 to 5 wt % | Dialkyltartaramide |

A typical water-based adhesive composition to which the dialkyltartaramide surfactants of the invention may be added would comprise in an aqueous medium 30 to 65 wt % of an adhesive composition containing the following components:

| Water-Based Adhesive | |
|---|---|
| 50 to 99 wt % | Polymeric Resin (SBR, VAE, Acrylic) |
| 0 to 50 wt % | Tackifier |
| 0 to 0.5 wt % | Defoamer |
| 0.5 to 2 wt % | Dialkyltartaramide |

A typical water-based photoresist developer or electronic cleaning composition to which the N,N'-dialkyltartaramide surfactants of the invention may be added would comprise the following components:

| Water-based Photoresist Developer | |
|---|---|
| 0.1 to 3 wt % | Tetramethylammonium Hydroxide |
| 0 to 4 wt % | Phenolic Resin |
| 88 to 99 wt % | Water |
| 10 to 5000 ppm | Dialkyltartaramide |

Examples 1–5 illustrate the synthesis of various N,N'-dialkyltartaramides of this invention. All N,N'-dialkyltartaramides were synthesized and then characterized by Nuclear Magnetic Resonance (NMR) spectroscopy. All tartaramides prepared ranged from ~50% to >99% pure.

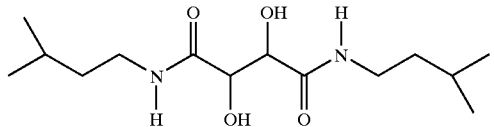

N,N'-Di-iso-pentyl L-tartaramide was prepared by the reaction of iso-pentyl amine with diethyl L-tartrate. To a round-bottomed flask were added diethyl L-tartrate (5.133 g, 1.0 eq), methanol (30 mL) and iso-pentyl amine (4.338 g, 2.0 eq). The clear light yellow solution was stirred for 16 hours at room temperature, after which point the methanol and ethanol were removed under vacuum with heating (<100° C.) (6.01 9, 84% yield).

EXAMPLE 2

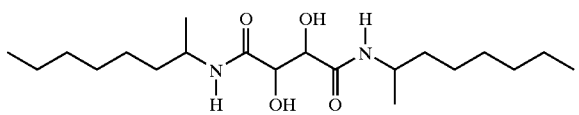

N,N'-Di-1-methylheptyl L-tartaramide was prepared by the reaction of 1-methyl-heptyl amine with diethyl L-tartrate. To a round-bottomed flask were added diethyl L-tartrate (10.008 g, 1 eq), methanol (32 mL), and 1-methylheptyl amine (12.548 g, 2.0 eq). The clear light yellow liquid was heated at 75° C. for 5.5 hours while removing methanol and ethanol. An orange wax was obtained (14.07 g, 78% yield). GC/MS results indicated that'smaller amounts of free amine, N-1-methylheptyl L-tartarimide, and the half ester/half amide intermediate were also present in addition to the desired product.

EXAMPLE 3

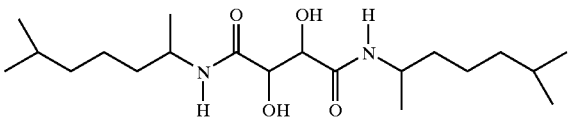

N,N'-Di-1,5-dimethylhexyl L-tartaramide was prepared by the reaction of 1,5-dimethylhexyl amine with diethyl L-tartrate. To a round-bottomed flask were added diethyl L-tartrate (10.036 g, 1 eq), methanol (32 mL), and 1,5-dimethylhexyl amine (12.589 9, 2.0 eq). The clear light yellow liquid was heated at 75° C. for 10 hours while removing methanol and ethanol. An orange viscous liquid was obtained (9.25 g, 51% yield). GC/MS results indicated that smaller amounts of free amine, N-1,5-dimethylhexyl L-tartarimide, and the half ester/half amide intermediate were also present in addition to the desired product.

EXAMPLE 4

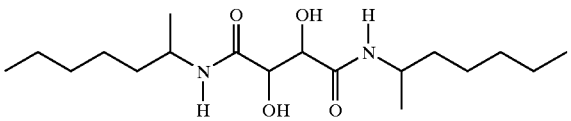

N,N'-Di-1-methylhexyl L-tartaramide was prepared by the reaction of 2-aminoheptane with diethyl L-tartrate. To a round-bottomed flask were added diethyl L-tartrate (10.020 g, 1 eq), methanol (32 mL), and 2-aminoheptane (11.198 g, 2.0 eq). After stirring for 24 hours at room temperature, the methanol and ethanol were removed under vacuum to yield a clear light yellow liquid. This liquid was heated at 60° C. for 8 hours and then heated to 70° C. for 8 hours while removing methanol and ethanol. An orange viscous liquid was obtained. GC/MS results indicated that smaller amounts of free amine, N-1-methylhexyl L-tartarimide, and the half ester/half amide intermediate were also present in addition to the desired product. $^{13}$C NMR confirmed the presence of several species, consistent with the $^{1}$H NMR and GC/MS results, and the amount of N,N'-di-1-methylhexyl L-tartaramide present in the mixture was calculated to be ~54% based upon integration of the 7 carbonyl carbon peaks.

EXAMPLE 5

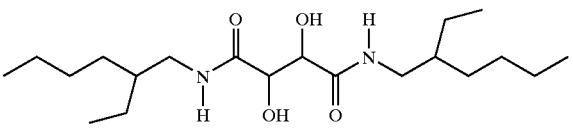

N,N'-Di-2-ethylhexyl L-tartaramide was prepared by the reaction of 2-ethylhexyl amine with diethyl L-tartrate.

Diethyl L-tartrate (19.147 g, 1.0 eq) and HPLC grade methanol (40 mL) were weighed into a 250 mL round-bottomed flask equipped with a teflon coated magnetic stir bar. 2-Ethylhexyl amine (24.005 g, 2.0 eq) was slowly poured into the stirring diethyl L-tartrate solution. Some fuming and a color change from water-white to pale yellow were observed. Additional methanol (10 mL) was used to rinse all of the amine into the reaction flask. After stirring the solution at ambient temperature overnight, the solvent was removed under vacuum with warming (<100° C.) to yield a viscous oil that solidified to a wax upon cooling (31.26 g, 83.9 mmole, 90% yield). The purity of the product was ~90%.

EXAMPLE 6

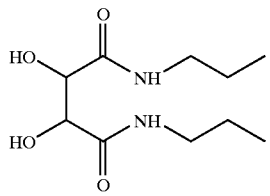

N,N'-Di-n-propyl L-tartaramide was prepared by the reaction of n-propyl amine with diethyl L-tartrate. Diethyl L-tartrate (20.027 g, 1.0 eq) and HPLC grade methanol (40 mL) were weighed into a 250 mL round-bottomed flask equipped with a teflon coated magnetic stir bar. n-Propyl amine (12.038 g, 2.0 eq) was slowly poured into the stirring diethyl L-tartrate solution. Some fuming and a color change from water-white to pale yellow were observed. Additional methanol (10 mL) was used to rinse all of the amine into the reaction flask. After stirring the solution for 30 min at ambient temperature, the product began to crystallize from solution. The reaction mixture was allowed to sit at ambient temperature for two hours. The flat, white crystals were filtered, washed with methanol (2×50 mL), washed with diethyl ether (2×30 mL), and dried under vacuum. The first crop of product was obtained in 35% yield (7.977 g, 34.34 mmole). Subsequently, a second crop of crystals (1.80 g, 7.75 mmole) was isolated from the mother liquor.

EXAMPLE 7

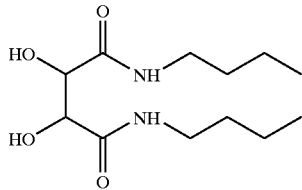

N,N'-Di-n-butyl L-tartaramide was prepared by the reaction of n-butyl amine with diethyl L-tartrate. Diethyl L-tartrate (20.010 g, 1.0 eq) and HPLC grade methanol (40 mL) were weighed into a 250 mL round-bottomed flask equipped with a teflon coated magnetic stir bar. n-Butyl amine (14.906 g, 2.0 eq) was slowly poured into the stirring diethyl L-tartrate solution. Some fuming and a color change from water-white to pale yellow were observed. Additional methanol (10 mL) was used to rinse all of the amine into the reaction flask. After stirring the solution for 30 min, the flask was stoppered and refrigerated at approximately 45° F. (7° C.). The product crystallized out after 30 min of refrigeration; however, it was allowed to remain in the refrigerator for 3 days. The white needle-like crystals were filtered, washed with methanol (~150 mL), washed with diethyl ether (2×30 mL), and dried under vacuum. The product was obtained in 56% yield (14.275 g, 54.8 mmole).

EXAMPLE 8

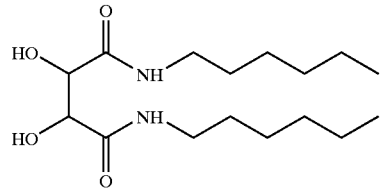

N,N'-Di-n-hexyl L-tartaramide was prepared by the reaction of n-hexyl amine with diethyl L-tartrate. Diethyl L-tartrate (20.007 g, 1.0 eq) and HPLC grade methanol (40 mL) were weighed into a 250 mL round-bottomed flask equipped with a teflon coated magnetic stir bar. n-Hexyl amine (20.614 g, 2.0 eq) was slowly poured into the stirring diethyl L-tartrate solution. Some fuming and a color change from water-white to pale yellow were observed. Additional methanol (10 mL) was used to rinse all of the amine into the reaction flask. The product precipitated after stirring the solution for 30 min at ambient temperature. The white, waxy solid was filtered, washed with methanol (3×30 mL), washed with diethyl ether (2×30 mL), and dried under vacuum. The first crop of product was obtained in 14% yield (4.366 g, 13.80 mmole). A second crop of product was obtained by adding the combined filtrates to 50 mL of water. After filtering, washing with diethyl ether (2×30 mL), and drying under vacuum, 9.382 g of white, waxy solid were obtained. The combined reaction yield was 45%.

EXAMPLE 9

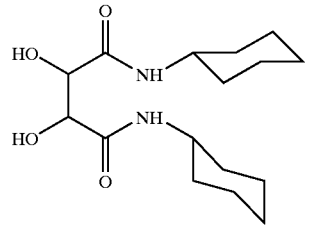

N,N'-Di-cyclohexyl L-tartaramide was prepared by the reaction of cyclohexyl amine with diethyl L-tartrate. Diethyl L-tartrate (19.997 g, 1.0 eq) and HPLC grade methanol (40 mL) were weighed into a 250 mL round-bottomed flask equipped with a teflon coated magnetic stir bar. Cyclohexyl amine (20.205 g, 2.0 eq) was slowly poured into the stirring diethyl L-tartrate solution. Some fuming and a color change from water-white to pale yellow were observed. Additional methanol (10 mL) was used to rinse all of the amine into the reaction flask. After stirring the solution for 30 min, the flask was stoppered and refrigerated at approximately 45° F. (70C). The product crystallized after 3 days at 45° F. (7° C.). The white crystals were filtered, washed with methanol (2×15 mL), and dried under vacuum. A first crop of 3.952 g (12.65 mmole, 13% yield) were obtained in this manner, and a second crop of 16.063 g were obtained by removing the solvent under vacuum. Overall yield was 66%.

EXAMPLES 10–18

Saturated solutions of the materials of Examples 1–9 in distilled water were prepared. After shaking the solutions for ~24 hours, the undissolved material was removed via filtration. Equilibrium surface tension (EST) data were obtained using the Wilhelmy plate method. Equilibrium surface tension values between 65–72 dyne/cm are considered to be indicative of a lack of surface activity (i.e., a lack of surfactancy).

The limiting equilibrium surface tension data are provided in Table 1. The limiting surface tensions represent the lowest surface tensions in water which can be achieved for a given surfactant regardless of the amount of surfactant used and is used to evaluate the effectiveness of a surfactant. Lower surface tensions would allow for the elimination of defects upon application of a formulation onto low energy surfaces.

TABLE 1

| Example | Compound | Limiting EST (dyne/cm) | Concentration of Surfactant in Solution |
|---|---|---|---|
| 10 | Di-isopentyl L-tartaramide (Ex 1) | 48.0 | <1.5 wt. % |
| 11 | Di-1-methylheptyl L-tartaramide (Ex 2) | 39.5 | <0.1 wt. % |
| 12 | Di-1,5-dimethylhexyl L-tartaramide (Ex 3) | 38.0 | <0.1 wt. % |
| 13 | Di-1-methylhexyl L-tartaramide (Ex 4) | 41.5 | <0.1 wt. % |
| 14 | Di-2-ethylhexyl L-tartaramide (Ex 5) | 41.4 | <0.1 wt. % |
| 15 | Di-n-propyl L-tartaramide (Ex 6) | 67.7 | <1.0 wt. % |
| 16 | Di-n-butyl L-tartaramide (Ex 7) | 65.0 | <1.0 wt. % |
| 17 | Di-n-hexyl L-tartaramide (Ex 8) | 67.8 | <0.1 wt. % |
| 18 | Di-cyclohexyl L-tartaramide (Ex 9) | 67.9 | <0.1 wt. % |

The data in Table 1 illustrate that certain N,N'-dialkyltartaramides have the ability to reduce the surface tension of aqueous compositions while others do not. Examples 10–14 demonstrate that N,N'-dialkyltartaramides containing branched C5–C8 alkyl groups exhibited surface tension values of less than 52 dyne/cm at a concentration of ≦1.5 wt % in water at 25° C. N,N'-Di-1-methylheptyl L-tartaramide (Ex 11), N,N'-di-1,5-dimethylhexyl L-tartaramide (Ex 12), N,N'-di-1-methylhexyl L-tartaramide (Ex 13), and N,N'-di-2-ethylhexyl L-tartaramide (Ex 14) are particularly effective at lowering the equilibrium surface tension of water. Therefore, the N,N'-dialkyltartaramides which contain branched alkyl groups with 5–8 carbon atoms are the most preferred for the reduction of surface tension of water in water-based, organic compound containing compositions, including waterborne coatings, inks, adhesives, fountain solutions, agricultural and electronic chemical formulations. However, ultimately the choice of N,N'-dialkyltartaramide will depend upon the application.

EXAMPLES 19–22

The foaming properties of aqueous solutions of N,N'-di-iso-pentyl L-tartaramide (Ex 1), N,N'-di-2-ethylhexyl L-tartaramide (Ex 5) and two representative nonionic surfactants, a commercial nonylphenol 15 mole ethoxylate surfactant and a commercial C8 alkyl glucoside surfactant, were examined using a procedure based upon ASTM D 1173–53. The results are reported in Table 2.

In this test, an aqueous mixture of the tartaramides was prepared, any undissolved solids were filtered off, and the filtrate was added from an elevated glass pipette to a glass receiver containing the same filtrate. Regarding the commercial materials, a 0.1 wt % solution of the surfactant was added from an elevated glass pipette to a glass receiver containing the same solution. The foam height was measured at the completion of the addition ("Initial Foam Height") and the time required for the foam to dissipate at the air-liquid interface ("Time to 0 Foam") was recorded. This test provides a comparison between the foaming characteristics of various surfactants. In general, in coatings, inks, adhesives, agricultural and electronics cleaning formulations, foam is undesirable because it complicates handling and can lead to coating and print defects, and to inefficient application of agricultural materials.

TABLE 2

| Ex | Surfactant | Initial Foam (cm) | Foam after 5 min (cm) | Time to zero foam |
|---|---|---|---|---|
| 19 | Di-isopentyl L-tartaramide (Ex 1) | 0.5 cm | 0 | ≦5 sec |
| 20 | Di-2-ethylhexyl L-tartaramide (Ex 5) | 1.5 cm | 0 | ~3 sec |
| 21 | Nonylphenol 15 mole ethoxylate | 5 cm | 4 cm | >5 min |
| 22 | C8 Alkyl glucoside | 1.9 cm | 1.0 cm | 37 min |

The data in Table 2 show that the compounds of this invention formed very little initial foam and that the foam which formed dissipated very quickly. In addition to their ability to reduce the surface tension of organic-containing aqueous systems, N,N'-dialkyltartaramide surfactants have desirable foam properties with respect to their use in coatings, inks, adhesives, fountain solution, agricultural and electronic chemical formulations.

The ability to control foam is advantageous in many applications, including coatings, inks, adhesives. fountain solutions, agricultural and electronic cleaning formulations. A drawback to the use of many conventional surfactants in these applications is the formation of considerable quantities of long-lasting foam in these systems. For such applications, it is desired that a surfactant form as little foam as possible and that the foam which forms dissipates quickly.

STATEMENT OF INDUSTRIAL APPLICATION

The invention provides compositions suitable for reducing the equilibrium surface tension in water-based coating, ink, adhesive, fountain solution, agricultural, electronic cleaning and photoresist developer compositions.

We claim:

1. In a method for applying a coating of a water-based composition to a surface to partially or fully coat the surface, the composition containing an inorganic or organic compound and an effective amount of a surfactant for reducing the equilibrium surface tension of the composition, the improvement which comprises employing as the surfactant an N,N'-dialkylamide of tartaric acid of the following structure:

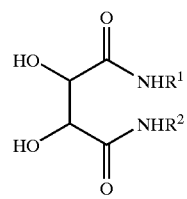

where $R^1$ and $R^2$ are C4 to C8 alky groups with at least one of $R^1$ and $R^2$ being a branched C4 to C8 alkyl group.

2. The method of claim 1 in which the water-based composition is selected from the group consisting of aqueous organic coating, ink, adhesive, fountain solution, agricultural and electronics cleaning compositions and the dialkyltartaramide is present at 0.001 to 20 wt % of the water-based composition.

3. The method of claim 2 in which an aqueous solution of the dialkyltartaramide demonstrates an equilibrium surface tension of less than 52 dynes/cm at a concentration of no more than 5 wt % in water at 25° C. according to the Wilhelmy plate method.

4. The method of claim 1 in which $R^1$ and $R^2$ are the same.

5. The method of claim 4 in which $R^1$ and $R^2$ are branched C6–C8 alkyl groups.

6. The method of claim 4 in which $R^1$ and $R^2$ are branched C8 alkyl groups.

7. The method of claim 4 in which the alkyl groups are 2-ethylhexyl.

8. The method of claim 4 in which the alkyl groups are 1-methylheptyl.

9. The method of claim 4 in which the alkyl groups are 1,5-dimethylhexyl.

10. The method of claim 7 in which the alkyl groups are 1-methylhexyl.

11. An aqueous composition comprising in water an inorganic compound which is a mineral ore or a pigment or an organic compound which is a pigment, a polymerizable monomer, an oligomeric resin, a polymeric resin, a detergent, a herbicide, an insecticide, a fungicide. or a plant growth modifying agent and an effective amount of an N,N'-dialkylamide of tartaric acid of the following structure for reducing the surface tension of the composition:

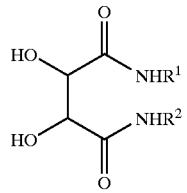

where $R^1$ and $R^2$ are C4 to C8 alkyl groups with at least one of $R^1$ and $R^2$ being a branched C4 to C8 alkyl group.

12. The aqueous composition of claim 11 in which an aqueous solution of the dialkyltartaramide demonstrates an equilibrium surface tension of less than 52 dynes/cm at a concentration of $\leq 5$ wt % in water at 25° C. according to the Wilhelmy plate method and the dialkyltartaramide is present at 0.01 to 10 wt % of the aqueous composition.

13. The aqueous composition of claim 12 in which $R^1$ and $R^2$ are branched C6 alkyl groups.

14. The aqueous composition of claim 12 in which $R^1$ and $R^2$ are branched C7 alkyl groups.

15. The aqueous composition of claim 12 in which $R^1$ and $R^2$ are branched C8 alkyl groups.

16. The aqueous composition of claim 15 in which the alkyl groups are 2-ethyl-hexyl.

17. The aqueous composition of claim 15 in which the alkyl groups are 1-methylheptyl.

18. The aqueous composition of claim 15 in which the alkyl groups are 1,5-dimethylhexyl.

19. The aqueous composition of claim 14 in which the alkyl groups are 1-methylhexyl.

20. The composition of claim 12 which is an aqueous organic coating composition comprising in an aqueous medium 30 to 80 wt % of a coating composition which comprises the following components 0 to 50 wt % pigment dispersant, grind resin or mixtures thereof;

0 to 80 wt % coloring pigment, extender pigment, anti-corrosive pigment, other pigment types or mixtures thereof;

5 to 99.9 wt % water-borne, water-dispersible or water-soluble resin or mixtures thereof;

0 to 30 wt % slip additive, antimicrobial agent, processing aid, defoamer or mixtures thereof;

0 to 50 wt % coalescing or other solvent;

0.01 to 10 wt % surfactant, wetting agent, flow and leveling agents or mixtures thereof; and 0.01 to 20 wt % dialkyltartaramide.

21. The composition of claim 12 which is an aqueous ink composition comprising in an aqueous medium 20 to 60 wt % of an ink composition which comprises the following components 1 to 50 wt % pigment;

0 to 50 wt % pigment dispersant, grind resin or mixtures thereof;

0 to 50 wt % clay base in a resin solution vehicle;

5 to 99 wt % water-borne. water-dispersible or water-soluble resin or mixtures thereof;

0 to 30 wt % coalescing or other solvent;

0.01 to 10 wt % processing aid, defoamer, solubilizing agent or mixtures thereof;

0.01 to 10 wt % surfactant, wetting agent or mixtures thereof; and 0.01 to 20 wt % dialkyltartaramide.

22. The composition of claim 12 which is an aqueous agricultural composition comprising in an aqueous medium 0.01 to 80 wt % of an agricultural composition which comprises the following components 0.1 to 50 wt % a herbicide, insecticide, plant growth modifying agent or mixtures thereof;

0.01 to 10 wt % surfactant;

0 to 5 wt % dye;

0 to 20 wt % thickener, stabilizer, co-surfactant, gel inhibitor, defoaming agent or mixtures thereof;

0 to 25 wt % antifreeze; and 0.01 to 50 wt % dialkyltartaramide.

23. The composition of claim 12 which is an aqueous fountain solution composition comprising the following components 0.05 to 10 wt % film formable, water soluble macromolecule;

1 to 25 wt % alcohol, glycol, or polyol with 2–12 carbon atoms which is water soluble or can be made water soluble;

0.01 to 20 wt % water soluble organic acid, inorganic acid, or a salt thereof;

30 to 70 wt % water; and 0.01 to 5 wt % dialkyltartaramide.

24. The composition of claim 12 which is an aqueous adhesive composition comprising in an aqueous medium 30 to 65 wt % of an adhesive composition which comprises the following components 50 to 99 wt % polymeric resin;

0 to 50 wt % tackifier;

0 to 0.5 wt % defoamer; and 0.5 to 2 wt % dialkyltartaramide.

25. The composition of claim 12 which is an aqueous electronics cleaning composition comprising in an aqueous medium the following components 0.1 to 3 wt % tetramethylammonium hydroxide;

0 to 4 wt % phenolic compound; and 10 to 10,000 ppm dialkyltartaramide.

* * * * *

UNITED STATES PATENT AND TRADEMARK OFFICE
CERTIFICATE OF CORRECTION

PATENT NO. : 6,399,543 B1
DATED : June 4, 2002
INVENTOR(S) : Ingrid Kristine Meier et al.

It is certified that error appears in the above-identified patent and that said Letters Patent is hereby corrected as shown below:

Column 12,
Line 60, delete "alky" and substitute therefor -- alkyl --

Column 13,
Line 21, delete "fungicide." and substitute therefor -- fungicide, --
Line 39, delete "$\leqq$ and substitute therefor -- $\leq$ --

Signed and Sealed this

Eighth Day of October, 2002

Attest:

Attesting Officer

JAMES E. ROGAN
Director of the United States Patent and Trademark Office